(12) United States Patent
Williams et al.

(10) Patent No.: US 6,755,784 B2
(45) Date of Patent: *Jun. 29, 2004

(54) METHODS FOR DELIVERING A DRUG TO A PATIENT WHILE RESTRICTING ACCESS TO THE DRUG BY PATIENTS FOR WHOM THE DRUG MAY BE CONTRAINDICATED

(75) Inventors: Bruce A. Williams, Flemington, NJ (US); Joseph K. Kaminski, Hampton, NJ (US)

(73) Assignee: Celgene Corporation, Warren, NJ (US)

( * ) Notice: Subject to any disclaimer, the term of this patent is extended or adjusted under 35 U.S.C. 154(b) by 34 days.

This patent is subject to a terminal disclaimer.

(21) Appl. No.: 10/383,275

(22) Filed: Mar. 7, 2003

(65) Prior Publication Data

US 2003/0149345 A1 Aug. 7, 2003

Related U.S. Application Data

(63) Continuation of application No. 09/965,155, filed on Sep. 27, 2001, now Pat. No. 6,561,977, which is a continuation of application No. 09/694,217, filed on Oct. 23, 2000, now Pat. No. 6,315,720.

(51) Int. Cl.$^7$ ............................................... A61B 5/00
(52) U.S. Cl. ........................................ 600/300; 128/920
(58) Field of Search ............................... 600/301, 300, 600/304; 395/200–210; 128/920, 925, 904, 897; 707/102; 706/23; 705/2–4; 235/375

(56) References Cited

U.S. PATENT DOCUMENTS

| | | | |
|---|---|---|---|
| 5,299,121 A | | 3/1994 | Brill et al. ................. 600/301 |
| 5,594,637 A | | 1/1997 | Eisenberg et al. .......... 600/300 |
| 5,619,991 A | | 4/1997 | Sloane ....................... 600/300 |
| 5,660,176 A | | 8/1997 | Iliff ........................... 600/300 |
| 5,845,255 A | | 12/1998 | Mayaud ........................ 705/3 |
| 5,974,203 A | | 10/1999 | Tadokoro et al. ........... 382/309 |
| 6,014,631 A | | 1/2000 | Teagarden et al. ............. 705/3 |
| 6,045,501 A | * | 4/2000 | Elsayed et al. ............. 600/300 |
| 6,055,507 A | | 4/2000 | Cunningham .................. 705/3 |
| 6,063,026 A | * | 5/2000 | Schauss et al. ............. 600/300 |
| 6,128,620 A | | 10/2000 | Pissanos et al. ............ 707/102 |
| 6,131,090 A | | 10/2000 | Basso, Jr. et al. ............ 706/23 |
| 6,202,923 B1 | * | 3/2001 | Boyer et al. ................ 235/375 |
| 6,315,720 B1 | | 11/2001 | Williams et al. ............ 600/300 |

FOREIGN PATENT DOCUMENTS

| | | |
|---|---|---|
| WO | WO 98/13783 | 4/1998 |
| WO | WO 99/10829 | 3/1999 |
| WO | WO 00/51053 | 8/2000 |

\* cited by examiner

*Primary Examiner*—Michael Astorino
(74) *Attorney, Agent, or Firm*—Woodcock Washburn LLP

(57) ABSTRACT

Methods for delivering a drug to a patients in need of the drug, while restricting access to the drug by patients for whom the drug may be contraindicated are disclosed. The methods are of the type in which prescriptions for the drug are filled by a pharmacy only after a computer readable storage medium has been consulted to retrieve a prescription approval code. Embodiments are provided wherein the patients are assigned to risk groups based upon the risk that taking the drug will lead to an adverse side effect, and certain additional information, such as periodic surveys and diagnostic tests probative of the ongoing risk of the side effect developing are obtained before prescriptions for the drug are approved.

34 Claims, No Drawings

METHODS FOR DELIVERING A DRUG TO A PATIENT WHILE RESTRICTING ACCESS TO THE DRUG BY PATIENTS FOR WHOM THE DRUG MAY BE CONTRAINDICATED

CROSS-REFERENCE TO RELATED APPLICATION

This application is a continuation of patent application Ser. No. 09/965,155, filed Sep. 27, 2001, now U.S. Pat. No. 6,561,977, which is a continuation of patent application Ser. No. 09/694,217, filed Oct. 23, 2000, now U.S. Pat. No. 6,315,720, the entirety of each of which is incorporated herein by reference.

FIELD OF THE INVENTION

The present invention relates to improved methods for delivering a drug to a patient. More particularly, the present invention relates to novel methods for delivering a teratogenic or other potentially hazardous drug to a patient in need of the drug, while avoiding the occurrence of known or suspected side effects of the drug. The novel methods permit the distribution to patients of drugs, particularly teratogenic drugs, in ways wherein such distribution can be carefully monitored and controlled.

BACKGROUND OF THE INVENTION

Many beneficial drugs are known or suspected of producing adverse side effects in certain individuals. These side effects may be manifest in the patient taking the drug, in a foetus (i.e. fetus) carried by the patient, or in a recipient (or foetus carried by a recipient) of the bodily fluids of the patient. In some cases, administration of the drug may be acceptable in some patients, but absolutely contraindicated in other patients. For example, drugs known or suspected of causing birth defects if taken by a pregnant woman (i.e. teratogenic drugs), may nonetheless be beneficial for treating certain conditions. However, because of the teratogenic properties of the drug, administration to pregnant women must be avoided. Other drugs are known which may be beneficially employed in the general population, but must be avoided by individuals having a certain preexisting condition, or those concurrently taking certain other medication(s), due to adverse side effects which may develop in those individuals.

One such drug which is known to produce adverse side effects, but which may nevertheless be beneficially employed in certain patients is thalidomide. Thalidomide is a drug which was first synthesized in Germany in 1957. Beginning in 1958, it was marketed in many countries for use as a sedative, although it was never approved for use in the United States. After reports of serious birth defects, thalidomide was withdrawn from all markets by 1962. However, during the years it was used, it was found to be effective in treating erythema nodosum leprosum (ENL), a condition of leprosy, and the U.S. Food and Drug Administration (FDA) has made the drug available for this specific use via a program of the Public Health Service. More recently, investigators have found that thalidomide may be effective in treating AIDS wasting and aphthous ulcers occurring in AIDS patients. In addition, treatments for other diseases, such as a number of neoplastic diseases including cancers, rheumatoid arthritis, and macular degeneration, are also believed to be possible. The FDA has recently approved an application by Celgene Corporation, which is the assignee of the present patent application, to market thalidomide for the treatment of ENL. The medical community anticipates that thalidomide will be used for treatment of additional conditions and diseases, including those set forth above. However, due to the severe teratogenic risk of thalidomide, methods are needed to control the distribution of this drug so as to preclude administration to foetuses.

In this regard, U.S. Pat. No. 6,045,501, to Elsayed et al., provides methods for delivering a drug to a patient while preventing the exposure of a foetus or other contraindicated individual to the drug. According to the methods of this patent, prescriptions for the drug are filled only after a computer readable storage medium has been consulted to assure that the prescriber is registered in the medium and qualified to prescribe the drug, that the pharmacy is registered in the medium and qualified to fill the prescription for the drug, and the patient is registered in the medium and approved to receive the drug. Improvements to this method may be useful, however, to minimize and simplify the demands on the pharmacy, thereby improving compliance with the system of distribution, and reducing the risk that the drug will be dispensed to a contraindicated individual.

Methods for monitoring and educating patients to whom a drug is distributed have been developed in connection with Accutane (isotretinoin). Accutane, which is a known teratogen, is a uniquely effective drug for the treatment of severe, recalcitrant, nodular acne. A pregnancy prevention program was developed, and the Slone Epidemiology Unit of Boston University designed and implemented a survey to evaluate these efforts. The survey identified relatively low rates of pregnancy during Accutane treatment, which suggests that such a program can be effective. With more than about 325,000 women enrolled to date in the Accutane survey, it is also clear that such a large-scale study can be conducted. Enrollment in the Accutane survey is voluntary, however. Accordingly, assessing the representativeness of the women who have been enrolled in the survey has been problematic, and it has been difficult to determine whether the survey results can be generalized to all female Accutane users. Thus, an improved survey is needed which would be representative of all users of a particular drug, such as thalidomide, who obtain the drug through legal distribution channels. There are also no mechanisms provided to assure compliance with the program or to limit distribution of the drug to participants in the survey.

Because drug sharing may frequently occur among AIDS patients, which may result in placing a foetus at risk, a program is needed which can be used to educate men and women about the risk of teratogenic drugs, such as thalidomide. In addition, a system is needed for the controlled distribution of a drug, in which of all users of the drug, including prescribers, pharmacies, and patients, may be accountable for their compliance with methods that may be established to minimize the risk that a contraindicated individual will be exposed to the drug. The present invention is directed to these, as well as other important ends.

SUMMARY OF THE INVENTION

The present invention is directed to improved methods for delivering a drug to a patient in need of the drug, while avoiding the occurrence of an adverse side effect known or suspected of being caused by the drug, of the type in which prescriptions for the drug are filled only after a computer readable storage medium has been consulted to assure that the prescriber is registered in the medium and qualified to prescribe the drug, that the pharmacy is registered in the medium and qualified to fill the prescription for the drug, and the patient is registered in the medium and approved to receive the drug. In one embodiment of the invention, there are provided improved methods comprising the steps of:

a. defining a plurality of patient risk groups based upon a predefined set of risk parameters for the drug;

b. defining a set of information to be obtained from the patient, which information is probative of the risk that such adverse side effect is likely to occur if the drug is taken by the patient;

c. in response to the information set, assigning the patient to at least one of the risk groups; and d. entering the risk group assignment in the medium before the patient is approved to receive the drug.

The improved methods described herein provide advantageous and effective means for monitoring, controlling and authorizing the distribution to patients of drugs known or suspected of causing adverse side effects. The methods of the present invention include a variety of checks and balances which serve to limit unauthorized and possibly inappropriate distribution of the drug. These methods are particularly applicable to distribution of teratogenic drugs, in which case the checks and balances may be particularly advantageous for preventing distribution of the drug to patients whose use of the drug may pose an unacceptable risk that a foetus carried by the patient or a recipient of the bodily fluids of the patient will be exposed to such drugs. Accordingly, the present methods may be advantageously used to avoid exposure of foetuses to teratogenic drugs, thereby avoiding the terrible birth defects which may result from such exposure.

The invention is not limited to the distribution of teratogenic drugs; other potentially hazardous drugs may also be distributed in accordance with embodiments of this invention and such drugs may be distributed in such a fashion that persons for whom such drugs are contraindicated will not receive them. These and other aspects of the invention will become more apparent from the present description and claims.

DETAILED DESCRIPTION OF PREFERRED EMBODIMENTS

The present invention is directed generally to methods for the delivery of drugs known or suspected of causing an adverse side effect, especially teratogenic drugs, to patients. The term "drug," as used herein, refers to any substance which is intended for use in the diagnosis, cure, mitigation, treatment or prevention of disease, or to affect the structure or function of the body. The term "side effect" refers to any abnormality, defect, mutation, lesion, degeneration or injury which may be caused by taking the drug. The side effect may be one which is likely to arise in the patient or in a foetus (i.e., fetus) carried by the patient. The side effect may also be one which is likely to arise in a recipient of the bodily fluid of the patient, or foetus carried by such recipient. The term "likely to arise" means that the side effect known or suspected of being caused by the drug may be expected to occur at a higher incidence rate in a particular individual or group of individuals.

Generally speaking, the methods of the present invention may be desirably and advantageously used to educate and reinforce the actions and behaviors of patients who are taking a drug, as well as prescribers who prescribe the drug and pharmacies which dispense the drug. As used herein, the term "prescriber" refers to any individual who is capable of prescribing drugs, including, for example, a medical doctor. Such education and reinforcement of actions and behavior are often necessary to ensure proper prescribing and dispensing of the drug, as well as patient compliance with taking the drug. A wide variety of educational materials may be employed to ensure proper prescribing, dispensing and patient compliance according to the methods described herein, including, for example, a variety of literature and other materials, such as, for example, product information, educational brochures, continuing education monographs, videotapes and the like which may describe the risks and benefits associated with taking the particular drug and measures which may be taken to avoid those risks.

The methods described herein may be advantageously employed to avoid delivery of one or more drugs known or suspected of causing an adverse side effect to a patient for whom the drugs may be contraindicated. As used herein, the term "contraindicated" refers to any condition in a patient which renders a particular line of treatment, including the administration of one or more drugs, undesirable or improper. This condition may be preexisting, or may develop while the patient is taking the drugs, including conditions which may result directly or indirectly from treatment with the drugs. Thus, contraindicated drugs include, for example, teratogenic drugs whose administration, for example, to pregnant patients is importantly avoided due to the risks to the foetus. Drugs may also be considered "contraindicated," as the term is used herein, if use of a drug by patients who are also taking another drug is known or suspected of producing an adverse side effect in those patients, or in a foetus carried by such patients.

The methods of the present invention are especially advantageously employed for the delivery to a patient of a teratogenic drug. The delivery of a teratogenic drug to a patient may be advantageously achieved with the present methods while substantially (including completely) avoiding the delivery of the drug to a foetus. The term "substantially," as used in reference to avoiding the delivery of a teratogenic drug to a foetus, generally means that there is an avoidance rate of delivering the drug to a foetus of greater than about 50%. Preferably, the avoidance rate is greater than about 55%, with an avoidance rate of greater than about 60% being more preferred. Even more preferably, the avoidance rate is greater than about 65%, with an avoidance rate of greater than about 70% being still more preferred. Yet more preferably, the avoidance rate is greater than about 75%, with an avoidance rate of greater than about 80% being still more preferred. In even more preferred embodiments, the avoidance rate is greater than about 85%, with an avoidance rate of greater than about 90% being yet more preferred. Still more preferably, the avoidance rate is greater than about 95%. In particularly preferred embodiments, a teratogenic drug may be delivered to patients with completely no delivery to foetuses (i.e., 100% avoidance rate).

The drug delivery methods of the present invention preferably involve, inter alia, registering in a computer readable storage medium prescribers who are qualified to prescribe the involved drug, including, for example, teratogenic drugs. Once registered in the computer readable storage medium, the prescriber may be eligible to prescribe the drug to patients in need of the drug. Generally speaking, in order to become registered in the computer readable storage medium, the prescriber may be required to comply with various aspects of the methods described herein including, for example, providing patient education and counseling, and the like, as described in detail below. The registration of the prescriber in the computer readable storage medium may be achieved by providing the prescriber, for example, by mail, facsimile transmission, or on-line transmission, with a registration card or form, preferably together with appropriate educational materials concerning, for example, the particular drug for which the prescriber is being registered to prescribe, as well as suitable methods for delivering the drug to the patient, including the drug delivery methods described herein. The prescriber will preferably complete the registration card or form by providing information requested therein, and the registration card or form will preferably be returned to the manufacturer or distributor of the drug, or other authorized recipient of the registration materials, for example, by mail, facsimile transmission or on-line transmission. Information which may be requested of the prescriber in the registration card or form may include, for example, the prescriber's name, address, and affiliation, if any with one or more health care institutions. The prescriber's information in the registration card or form is then entered into the computer readable storage medium. It is contemplated that the registration of the prescriber into the computer readable storage medium may also be achieved, for example, by telephone, and/or through the use of an integrated voice response system. Suitable computer readable storage media which may be employed for registration of the prescribers (as well as the pharmacies and patients, as discussed below) will be apparent to one of ordinary skill in the art, once armed with the teachings of the present application.

In accordance with the methods described herein, pharmacies who are qualified to fill prescriptions for the particular drug being prescribed including, for example, teratogenic drugs, are also preferably registered in a computer readable storage medium. The computer readable storage medium in which the pharmacies are registered may be the same as, or different from the computer readable storage medium in which the prescribers are registered. Once registered in the computer readable storage medium, the pharmacies may be eligible to dispense the involved drug to patients who are in need of the drug. Generally speaking, in order to become registered in the computer readable storage medium, the pharmacy may be required to comply with various aspects of the methods described herein including, for example, registering the patient (preferably also in a computer readable storage medium), ensuring that the patient complies with certain aspects of the drug delivery methods, as well as other aspects of the present methods, as described in detail below. As with the registration of the prescriber in the computer readable storage medium, the registration of the pharmacy may be achieved by providing the pharmacy, for example, by mail, facsimile transmission, or on-line transmission, with a registration card or form, preferably together with appropriate educational materials concerning, for example, the particular drug for which the pharmacy is being registered to dispense, as well as suitable methods for delivering the drug to the patient, including the drug delivery methods described herein. The pharmacy may then have the registration card or form completed by providing the information requested therein, which thereafter may be returned to the manufacturer or distributor of the drug, or other authorized recipient of the registration card or form, for example, by mail, facsimile transmission or on-line transmission. Information which may be requested of the pharmacy in the registration card or form may include, for example, the pharmacy's name, address, and affiliation, if any, with any health care institution such as, for example, a hospital, health care organization, and the like. The pharmacy's information in the registration card or form is then preferably entered into the computer readable storage medium. It is contemplated that the registration of the pharmacy into the computer readable storage medium may also be achieved, for example, by telephone and/or through the use of an integrated voice response system.

As noted above, the drug delivery methods described herein also preferably involve the registration of the patient in a computer readable storage medium. The computer readable storage medium in which the patients are registered may be the same as, or different from the computer readable storage medium in which the prescriber and/or pharmacy is registered. Generally speaking, in order to become registered in the computer readable storage medium, the patient may be required to comply with various aspects of the methods described herein. The registration of the patient may be carried out by the registered pharmacy, for example at the time of the patient's initial visit to the pharmacy. It has been found, however, that it may be more efficient, and better compliance with the methods of the present invention may be provided, if registration of the patient is carried out by the registered prescriber of the drug at the time the initial prescription is generated.

In preferred form, the prescriber will typically have a registration card or form filled out for the patient, which includes information on the patient, such as the patient's name, sex, mailing address, date of birth, and the like. Information on the prescribing prescriber and dispensing pharmacy, such as the information described above for the registration thereof, may also be desirably entered on the patient registration card or form. The completed card or form may then be forwarded to the manufacturer or distributor of the drug, or other authorized recipient of the registration form, for example, by mail, facsimile transmission or on-line transmission. Where registration is by mail or facsimile, entry of the registration into the computer readable storage medium may preferably include the use of optical character recognition (OCR) software. It is also possible that the registration of the patient into the computer readable storage medium may also be achieved, for example, by telephone and/or through the use of an integrated voice response system.

Preferably, information will also be collected from the patient that may be probative of the risk that a known or suspected side effect will occur if the drug is taken by the patient. This information may then be compared with a predefined set of risk parameters for the drug, which in turn define a plurality of risk groups, so that analysis of the information will permit assignment of the patient to at least one of the risk groups. Preferably, this risk group assignment is then also entered into the computer readable storage medium. This assignment may be performed by the prescriber, who may then include the risk group assignment on the patient's registration card or form, or may be performed by another individual, such as a nurse, technician, or office personnel, who preferably interprets the information and assigns the patient to one of the risk groups, accordingly.

As discussed above, it is preferable that a plurality of risk groups, each based upon a predefined set of risk parameters, be established for the drug which is to be administered. As will be evident to those of skill in the art, the risk parameters to be considered and the risk groups defined by those parameters, will be based upon factors which influence the risk that a known or suspected adverse side effect will occur if the patient receives the drug, and will vary depending upon the drug in question. Where the drug is a teratogenic drug, for example, such risk parameters may include elements which would impact the risk of a foetus being exposed to the drug, such as the age, sex and reproductive status of the patient. For example, a first risk group may comprise female patients of child bearing potential; a second risk group may comprise female patients of non-child bearing potential; a third risk group may comprise sexually active male patients; and a fourth risk group may comprise sexually inactive male patients. Additionally, there may be a risk group established for patients to whom administration of the drug may be strictly contraindicated, and patients assigned to such a group will not be approved to receive the drug. For other drugs, different factors, such as those influencing the likelihood that certain preexisting conditions may exist, or the likelihood of certain other drugs being used concomitantly with the prescribed drug, may define the relevant risk parameters.

By assigning each patient to a risk group, the steps that will be taken to minimize the chance that the drug is dispensed to a contraindicated patient, and to minimize the risk that a known or suspected adverse side effect will occur, can be tailored to suit the circumstances of that particular patient. For example, depending upon which risk group a patient is assigned to, additional information may be collected from the patient. As discussed more fully below, such additional information may be in the form, for example, of a patient survey. Such additional information may also include the results of certain diagnostic tests which have been performed. Based upon the additional information, the patient's risk group assignment may then remain the same, or the patient may be assigned to a different risk group, which may in turn require that further additional information be collected from the patient.

In accordance with the present invention, the monitoring of two, three or more drugs either administered to or proposed for administration to a patient may also be accomplished in order to avoid or diminish the likelihood of the occurrence of one or more side effects. Thus, combinations of drugs which, when administered to an individual patient, may give rise to an increased likelihood of side effects, may be registered in a computer readable storage medium, and the patient's risk group assignment may be reflective of this increased risk. A physician is registered to prescribe at least one of the drugs for a patient and a pharmacy is registered to fill such prescription. In this way, through assignment of such patient to one or more risk groups, the avoidance of harmful drug interactions may be attained.

It is preferred that for any given risk group, there may be defined a predetermined additional set of information which is to be collected from the patient. This additional set of information may be obtained prior to the initial dispensation of the drug to the patient and/or may be obtained from the patient on a periodic basis. This information may include information not previously obtained from the patient, or may simply reiterate previously asked questions, and repeat diagnostic tests which were conducted previously. The information may relate to the patient's conduct, or may relate to the patient's past or ongoing medical treatment, such as other procedures or medication which the patient may have received or is still receiving. For example, the additional set of information may be in the form of a survey or questionnaire regarding the patient's behavior and compliance with risk avoidance measures and may thus be probative of whether the risk of occurrence of an adverse side effect has increased, decreased or remained the same. Based upon the responses by the patient, the patient's risk group assignment may, if appropriate, be changed accordingly. Alternatively, where side effects which are known or suspected of being caused by a combination of drugs, the questions asked of the patient may be probative of the likelihood that the patient may take such a combination of drugs. Similarly, where sharing of drugs by the patient may be a matter of concern, the survey may be probative of the risk that the patient may be sharing the hazardous drug with another, and hence increase the risk that a contraindicated individual may receive the drug.

The additional information may also include the results of certain diagnostic tests which have been performed on the patient. Such diagnostic tests may be probative, for example, of the risk of exposure of a foetus to a teratogenic drug, may test for the presence of a risk factor for the adverse side effect of concern, or may be probative of the onset of that side effect. Where the use of combinations of more than one drug are known or suspected of causing an increased risk of the occurrence of a side effect, the diagnostic testing may include testing for the presence of one or more of those drugs, or evidence of the use by the patient of such other drugs. Additionally, diagnostic tests may be probative of the concentration of one or more drugs, including the prescribed drug or drugs, to assure that appropriate dosing is maintained.

Such diagnostic testing may be conducted on any bodily fluid or waste product of the patient, including the blood, serum, plasma, saliva, semen or urine, as well as the feces. Diagnostic testing may also be performed on a biopsy of any tissue of the patient or may include genetic testing, which may be indicative of a genetic predisposition to a particular adverse side effect. Other forms of diagnostic testing, such as diagnostic imaging, or tests which may be probative of the proper functioning of any tissue, organ or system are also contemplated. Preferably, the additional information and/or diagnostic test results are obtained and entered in the computer readable storage medium before the patient is approved to receive the drug. Additionally, where the information indicates that the risk of the adverse side effect occurring outweighs the potential benefit of the drug, the patient may be assigned to a risk group that will preclude approval of dispensation of the drug to that patient.

In accordance with the methods of the present invention, therefore, the delivery of the drug to the patient may involve the following steps. As a prelude to prescribing and dispensing the drug to the patient, the prescriber and the pharmacy are registered in one or more appropriate computer readable storage media, as described above. If the prescriber is not registered in the computer readable storage medium, the prescriber will be ineligible to prescribe the drug. Similarly, if the pharmacy is not registered in the computer readable storage medium, the pharmacy will be ineligible to dispense the drug.

In the course of an examination of a patient, including patients suffering from one or more diseases and/or disorders such as, for example, erythema nodosum leprosum (ENL), the prescriber may determine that the patient's condition would be improved by the administration of a drug such as, for example, a teratogenic drug, including thalidomide. Prior to prescribing the drug, the prescriber preferably counsels the patient, for example, on the various risks and benefits associated with the drug. For example, the prescriber preferably discusses the benefits associated with taking the drug, while also advising the patient on the various side effects associated therewith. In embodiments of the invention wherein the prescriber assigns the patient to a specific risk group, the disclosure is preferably tailored to that risk group assignment. Thus, a patient who may acquire or impart a condition or disease for which the drug is contraindicated is preferably counseled by the prescriber on the dangers associated therewith and advised as to risk avoidance measures which may be instituted. Preferably the patient is provided full disclosure of all the known and suspected risks associated with taking the drug. For example, in the case of teratogenic drugs, the prescriber preferably counsels the patient on the dangers of exposing a foetus, either one which may be carried by the patient or one carried by a recipient of the bodily fluids of the patient, to the teratogenic drug. Such counsel may be provided verbally, as well as in written form. In preferred embodiments, the prescriber provides the patient with literature materials on the drug for which a prescription is contemplated, such as product information, educational brochures, continuing education monographs, and the like. Thus, in the case of methods involving teratogenic drugs, the prescriber preferably provides patients with literature information, for example, in the form of the aforesaid product information, educational brochures, continuing education monographs, and the like, warning the patient of the effects of the drug on foetuses. In the case of other drugs which are known or suspected of causing an adverse side effect, the patient is counseled as to the dangers of taking the drugs, and of steps which may be taken to avoid those risks. For example, if the concomitant use of the drug and another drug, for example alcohol, is to be avoided, the prescriber advises the patient of the risks of drinking alcohol while taking the drug.

With particular reference to counseling provided in connection with teratogenic drugs, the prescriber preferably counsels female patients that such drugs must never be used by pregnant women. If the patient is a female of child-bearing potential (i.e., a woman who is capable of becoming pregnant), the prescriber preferably counsels the patient that even a single dosage of certain teratogenic drugs, such as thalidomide, may cause birth defects. Accordingly, the patient is preferably counseled to avoid sexual intercourse entirely, or if sexually active, to use appropriate forms of contraception or birth control. For both male and female patients, the prescriber preferably provides counsel on the importance of using at least two forms of effective birth control methods, with one form preferably being a highly effective hormonal method, and the other form preferably being an effective barrier method. The patients are preferably counseled to use the birth control methods for a period of time prior to and during treatment with the teratogenic drug, as well as for a period of time after treatment with the drug has been terminated. In preferred embodiments, the patient is counseled to use at least two forms of birth control for at least about 4 weeks prior to initiation of treatment, during treatment, and for at least about 4 weeks after treatment has been terminated. It may be desirable for the prescriber to personally provide female patients who are capable of becoming pregnant with one or more contraceptive devices or formulations.

Male patients who are being prescribed a teratogenic drug are preferably counseled to use condoms every time they engage in sexual relations, since many teratogenic drugs may be found in semen. Male patients are also preferably counseled to contact their prescriber if they have sexual intercourse without a condom, and/or if it is believed that they may have caused a pregnancy. As with female patients, it may be desirable for the prescriber to provide male patients who are capable of impregnating female patients with a contraceptive device or formulation. Other advice relative to birth control that the prescriber may provide to the patient would be apparent to one skilled in the art, once armed with the teachings of the present application. If the prescriber who is prescribing the teratogenic drug is unaware of certain aspects of the available forms of birth control and the advantages and disadvantages associated therewith, the patient should be referred to a prescriber who is knowledgeable on such matters, prior to be being prescribed the involved drug. Generally speaking, as discussed below, counseling on teratogenecity, birth control, and the like is preferably given only to female patients who are capable of becoming pregnant, or to male patients who are capable of having sexual relations with partners who are or can become pregnant. In this manner, unnecessary counseling, for example, to women who are no longer of child-bearing age or men who are incapable of sexual relations with such women, may be avoided.

With further reference to methods involving teratogenic drugs, it is also preferred that the prescriber advise the patient to not share the drug with anyone else, and particularly that the drug should be kept out of the reach of children as well as women of child-bearing potential. In the case of female patients, particularly female patients of child-bearing potential, the prescriber should give the patient a pregnancy test, preferably a serum pregnancy test, prior to and during treatment with the teratogenic drug. To begin receiving the teratogenic drug and to continue taking the drug, female patients of child-bearing potential should continue to have negative pregnancy tests. The patient is also preferably counseled by the prescriber to discard or return to the prescriber, pharmacy, manufacturer or distributor any unused portion of the prescribed drug.

As would be apparent to one of ordinary skill in the art, once armed with the teachings of the present application, one or more aspects of the counseling described above may be applicable, in certain circumstances, for drugs other than teratogenic drugs.

In addition to receiving counseling on the drug being prescribed, including counseling, for example, on birth control, and prior to receiving a prescription for the drug, the methods of the present invention preferably involve requiring the patient to fill out an informed consent form which is signed by the prescriber, as well as the patient. The prescriber should retain a copy of the informed consent form for his/her records. Verification that the patient has given his/her informed consent may also be registered in the computer readable storage medium. Preferably, this verification is provided by the prescriber, and may be included, for example, with the patient registration information and risk group assignment. It has surprisingly been found that by having the prescriber, rather than the pharmacy, verify the patient's informed consent, the methods of the present invention may operate more efficiently, leading to better compliance, and hence decreased risk that the adverse side effect will occur, may be achieved.

By filling out and signing an informed consent form, the patient acknowledges that he/she understands the risks associated with taking the drug. In the informed consent form, the patient preferably agrees to comply with the risk avoidance measures provided, and to behave in a manner which is consistent with the prescriber's counsel. For example, in cases involving, for example, teratogenic drugs, the patient may agree to use at least one form of birth control, with female patients agreeing to use at least two forms of birth control. In preferred embodiments, where the patient's risk group assignment so dictates, the patient will agree to undergo periodic diagnostic testing relevant to the risk that the adverse side effect to be avoided may occur or be occurring. In preferred embodiments involving teratogenic drugs, female patients preferably agree also to undergo pregnancy testing, preferably serum pregnancy testing, before, during and after treatment with the teratogenic drug.

Female patients preferably will also acknowledge that, at the time they are being prescribed the drug, especially teratogenic drugs, they are not pregnant, they will immediately stop taking the drug if they become pregnant, and they will not try to become pregnant for at least 4 weeks after treatment with the drug is terminated. Female patients, especially female patients for whom a teratogenic drug will be administered, preferably further agree to contact their prescriber if they wish to change one or more of the birth control methods being used and to have an additional pregnancy test if a menstrual period is missed. Female patients, especially female patients to be treated with teratogenic drugs, will preferably agree also to not breast-feed while being treated with the drug.

Male patients who are being prescribed the drugs according to the methods described herein, especially teratogenic drugs, will preferably agree to avoid having unprotected sexual relations with a woman, particularly a woman of child-bearing potential during treatment with the drug. In doing so, male patients will preferably further agree to use a condom during sexual relations with a woman, with latex condoms being preferred. Both male and female patients will also preferably agree to not share the drug with anyone, and to acknowledge that they cannot donate blood while taking the drug, with male patients agreeing also to not donate sperm while taking the drug. In addition, the patients will preferably agree to take part in a confidential patient survey, for example, before, during and after treatment with the drug. The patient survey provides information, for example, to the prescriber, manufacturer and/or distributor of the drug, as well as any group or body which may be established to generally provide oversight on the distribution of the drug, on information regarding the general lifestyle of the patient, including detailed information on the patient's sexual behavior. In this manner, the survey may assist in identifying patients who engage in risky behavior, as well as patients who are non-compliant with the methods described herein. Such risky behavior and/or non-compliance may lead to a suspension or intervention of the patient's treatment with the drug, with re-education being provided to the patient.

The information obtained from the survey is preferably also entered into the computer readable storage medium. Once entered into the computer readable storage medium, the prescriber, manufacturer and/or distributor of the drug may be able to glean therefrom information regarding the level of risk associated with the administration of the involved drug to the various patients. Accordingly, it may be possible to identify, from among the entire population of registered patients, one or more subpopulations of patients for which the involved drug may be more likely to be contraindicated. For example, it may be possible to identify a subpopulation of female patients who are capable of becoming pregnant and/or a subpopulation of male patients who are capable of impregnating female patients. Preferably, the counseling information discussed above relating to exposure of a foetus to a teratogenic drug may then be addressed primarily to this subpopulation of patients.

If the risk is considered to be acceptable, the patient may continue to receive the drug, using the methods described herein. If the risk is considered to be unacceptable, additional counseling may be provided to the patient or, if necessary, treatment of the patient with the involved drug may be terminated, with alternate treatment modalities being provided. In preferred embodiments, female patients will agree to complete a patient survey at least once every month, with male patients agreeing to complete a patient survey at least once every three to six months. The survey may be conducted by mail, facsimile transmission, on-line transmission or by telephone. Preferably, the survey is conducted by telephone through the use of an integrated voice response system (IVR).

After the patient has received counseling as described above, and has also filled out and signed an informed consent form, and it is determined that the drug which is to be prescribed is not contraindicated for the patient (such as, for example, a negative pregnancy test in the case of female patients for whom a prescription is desired for a teratogenic drug), the prescriber may prescribe the drug to the patient. In preferred embodiments of the present invention, the amount of the drug which is prescribed to the patient is for a limited amount, preferably no more than about 28 days. Refills for the drug will not be permitted without a renewal prescription from the prescriber, as discussed in detail below. In order to have the prescription filled, the patient preferably presents the prescription and the informed consent form to a pharmacy who has been registered, as discussed above. It is contemplated that the patient may bring the prescription to an unregistered pharmacy. If so, the pharmacy may take steps to become registered, for example, by immediately contacting the manufacturer of the drug. Once registration of the pharmacy is completed, the distribution procedure described herein may resume, per the discussion hereinafter. Of course, this may introduce a delay into the prescription process, and the patient may desire to take the prescription for the drug to an alternate, registered pharmacy. If the patient does not present a completed informed consent form to the pharmacy, or if verification of such informed consent has not previously been registered in the computer readable storage medium, the prescription may not be filled. In this case, pharmacy may contact the prescribing prescriber to have an informed consent form filled out for the patient.

The drug is preferably supplied to the pharmacy (as well as the patient) in packaging, such as individual blister packs, which includes warnings regarding the risks associated with the drug, as well as the importance of various aspects of the present methods such as, for example, pregnancy testing and the use of contraception (in the case of teratogenic drugs), and the dangers associated with sharing the drug with others, among other aspects.

As noted above, the drug is preferably prescribed and dispensed to the patient in a limited amount, with a prescription amount of no more than about 28 days being preferred, and preferably with no refills being permitted. Thus, for the patient to obtain an additional prescription, it is generally necessary for the patient to have a follow-up visit with the prescriber. Such a follow-up visit preferably takes place at least each time the patient requires a renewal of the prescription, and possibly more often if the patient requires, for example, additional counseling. At the follow-up visit, the patient will preferably receive additional counseling regarding the risks and benefits associated with taking the drug, as well as further counseling on birth control (if applicable). The patient will also preferably complete an additional patient survey to provide current information regarding their lifestyle, including their sexual behavior and, if female of childbearing potential, be administered a new pregnancy test. After receiving the counseling and completing the patient survey, and if the pregnancy tests for female patients are negative, the prescriber may fill out a new prescription for the drug. As with the original prescription, the renewal prescription is preferably for a limited period of time, with no more than about 28 days being more preferred.

In certain embodiments, the prescriber may also receive reminders, for example, via mail, facsimile, or on-line transmission, from the manufacturer, distributor or other group or body providing oversight on drug distribution, that the prescriber has prescribed a hazardous drug to patients which may be contraindicated, and that the involved patients may require additional counseling and diagnostic testing. Such reminders may preferably be delivered to the prescriber, for example, from about 14 to about 21 days after the previous prescription was filled.

As with the original prescription from the prescriber, the patient should present all renewal prescriptions to a registered pharmacy. Prior to filling out the prescription and dispensing the drug, the pharmacy preferably confirms, for example, via a standard on-line transmission or via telephone via IVR that the patient has been registered and is eligible to receive the drug. When patient eligibility has been confirmed, the pharmacy may dispense the drug to the patient. If the patient is ineligible, the pharmacy generally may not dispense the drug to the patient. The pharmacy may then contact, for example, the prescribing prescriber or the manufacturer of the drug to initiate patient registration. In preferred form, the pharmacy will be precluded from dispensing the drug if the patient has more than about 7 days of drug supply from the previous prescription, and/or if the new prescription was written more than about 14 days before the date the patient visits the pharmacy to have it filled.

The registration into one or more computer readable storage media of the prescriber, pharmacy and patient, according to the methods described herein, provide a means to monitor and authorize distribution of contraindicated drugs, including teratogenic drugs. Thus, the computer readable storage media may serve to deny access to, dispensing of, or prescriptions for contraindicated drugs, including teratogenic drugs, to patients, pharmacies or prescribers who fail to abide by the methods of the present invention. As noted above, prescribers who are not registered in a computer readable storage medium generally may not prescribe the drug, and pharmacys who are not registered generally may not dispense the drug. Similarly, the drugs generally may not be prescribed and/or dispensed to patients who are not registered in a computer readable storage medium. In addition, patients may be required to present an informed consent form to the pharmacy. Unless such a form is presented to the pharmacy, or verification of such informed consent has been provided by the prescriber and registered in the computer readable media, the patient generally may not receive the prescription for the drug. As noted above, only limited amounts of the drug may be prescribed to the patient, with no refill prescriptions being permitted.

In certain embodiments of the invention, the methods may require that the registered pharmacy consult the computer readable medium to retrieve a prescription approval code before dispensing the drug to the patient. This approval code is preferably not provided unless the prescriber, the pharmacy, the patient, the patient's risk group and the patient's informed consent have been properly registered in the storage medium. Additionally, depending upon the risk group assignment, generation of the prescription approval code may further require the registration in the storage medium of the additional set of information, including periodic surveys and the results of diagnostic tests, as have been defined as being relevant to the risk group assignment. Thus, to comply with the present methods and receive approval to dispense the drug as prescribed, the registered pharmacy need only retrieve the approval code. If the prescription approval code is not forthcoming, the patient may be directed to complete the necessary survey, for example, by telephone, or may be directed back to the prescriber for completion of necessary diagnostic tests. In this manner, the effort required by the pharmacy is minimized, and greater compliance with the present methods may efficiently and advantageously be achieved. Additionally, the embodiments described herein may provide greater assurance that all required further information, as is appropriate to the patient's risk group assignment, has been obtained before the drug is dispensed to the patient, and thereby minimize the risk that an adverse side effect will occur.

While the delivery of teratogenic drugs is an aspect of the present invention which has clearly apparent benefit, other types of drugs may also beneficially be prescribed and delivered in accordance with one or more embodiments hereof and all are contemplated hereby. For example, the methods of the present invention may be used for delivery of a drug which is known or suspected of causing liver damage in many patients who take the drug. One such drug is isoniazid, a widely known treatment for tuburculosis (TB). In following a method of the present invention, a registered physician may wish to prescribe isoniazid to a patient who has tested positive for TB. The physician may register the patient in a computer readable storage medium, along with certain information regarding the patient's age, medical condition, and so on. If the patient is a young adult, for example, and presents with no other complicating risk factors, the patient may be assigned to a risk group that is designated to receive counseling regarding certain behavior, such as the concomitant use of alcohol, that is to be avoided. The patient may be fully informed of the risks of liver damage that may result from taking isoniazid, and is preferably counseled to avoid drinking any alcoholic beverages while undergoing treatment with the drug. Preferably, the patient signs an informed consent form, and the prescribing physician transmits verification of the informed consent, along with the patient's registration form and risk group assignment to the computer readable storage medium. The physician then provides the patient with a prescription for the isoniazid. Upon presentation of the prescription to a registered pharmacy, the computer readable storage medium is consulted to verify that the patient and prescriber are registered therein, and that the patient's risk group assignment and informed consent have been provided.

If the patient's risk group assignment so indicates, certain diagnostic tests may additionally be required, so that baseline data may be obtained, before the prescription will be approved for filling. The patient's risk group may indicate, for example, that serum liver enzymes should be evaluated on a monthly basis. Under these circumstances, the prescription will preferably be filled for no more than about 30 days.

The patient will also preferably be advised that completion of a monthly survey will be required. This survey may include a questionnaire which is probative of the patient's alcohol consumption over the past month. The survey may also include questions which are probative of certain symptoms which may be indicative of the early onset of liver damage or other side effects known or suspected of being caused by isoniazid. Additionally, questions regarding the patient's concomitant use of other drugs which are known to be hazardous when taken in combination with isoniazid, may be asked. Preferably, this survey is conducted telephonically, using an integrated voice response system, and the responses are entered in the storage medium. Based upon the patient's responses, the patient's risk group assignment is adjusted or left the same, as may be appropriate.

The patient is preferably further instructed that periodic diagnostic testing may also be necessary for continued approval of a prescription. Preferably, the diagnostic testing will include an assay of the patient's serum liver enzyme levels, to screen for early signs of liver damage. Additionally, the diagnostic testing may include screens for the presence of other drugs known to also cause liver damage, or to be hazardous if taken in combination with isoniazid. A prescription approval code generally will not be generated for subsequent prescriptions or refills until such periodic tests have been performed and satisfactory results entered into the computer readable storage medium. If a prescription approval code is not received by the pharmacy, the patient is directed to complete the requisite survey or tests, or to return to the doctor for further consultation.

If the test results or survey indicate that the risk of liver damage has increased, the patient's risk group assignment may be changed, or the patient will be directed to consult with the prescriber before any further isoniazid may be dispensed. In this way, the development of the adverse side effect of concern may be monitored. For example, if the tests indicate that some liver enzymes are marginally elevated, the patient's risk group status may be changed from a first risk group to a second risk group. As a member of this second risk group, the patient may be required to undergo additional diagnostic testing before approval will be given to receive the drug. Such testing may include, for example, liver function tests, to further diagnose the level of cellular damage potentially being caused by the isoniazid, or the combination of isoniazid and other drugs, such as alcohol. In more extreme cases, a diagnostic ultrasound of the liver, or even a liver biopsy may even be indicated. Ultimately, if the risk of continued administration becomes so great that it outweighs the possible benefits of continued treatment with isoniazid, the patient may be assigned to a risk group which indicates that the drug may no longer be dispensed to that patient.

The methods of the present invention may similarly be employed, for example, where the patient is undergoing treatment for infection with the Human Immunodeficiency Virus (HIV). Patients who test positive for HIV may be treated with one or more drugs to combat the onset of the Acquired Immune Deficiency Syndrome (AIDS). Frequently, HIV positive patients are administered an "AIDS cocktail" of several drugs including, for example, a combination of one or more inhibitors of viral protease and reverse transcriptase. By following the methods of the present invention, the patient may continue to receive the combination of drugs, while the risk of adverse side effects from administration of the drugs may be minimized. Additionally, the methods of the present invention may be desirably and advantageously used to educate and reinforce the actions and behaviors of patients who are taking a drug, as well as prescribers who prescribe the drug and pharmacies which dispense the drug.

As with methods of the invention previously described, when a patient has tested positive for HIV, a registered prescriber may obtain background information on the patient and see that a registration form is completed so that the patient may be registered in the computer readable storage medium. The prescriber may prescribe one or more drugs to the patient, including drugs which may be known or suspected of causing adverse side effects, either alone or in combination with each other or with other drugs. Depending upon the drugs prescribed, and also upon information which the prescriber will preferably obtain regarding the patient's medical history, physical condition and lifestyle, the patient will preferably be assigned to at least one risk group. Based upon this risk group assignment, the patient will preferably receive educational materials and counseling regarding the risks associated with the prescribed drugs, and be advised of the importance of the treatment regimen. The patient will also preferably receive counseling regarding the risk of spreading the disease to others, including a foetus which may be carried by the patient and any recipient of a bodily fluid of the patient. Thus, the patient may be counseled regarding the preferential use of one or more methods of birth control, and may also be provided with a contraceptive device by the prescriber. Additionally, the patient will preferably be counseled not to share any of the drugs with others, and to avoid taking any medications not prescribed. In this way, the patient will preferably be counseled both as to methods for minimizing the spread of the disease, as well as to methods for avoiding the occurrence of one or more side effects which may result from the taking of the medication. Preferably, upon full disclosure of all risks inherent in the treatment regimen, the prescriber will obtain and register in the computer readable storage medium the informed consent of the patient to receive the medication and to comply with the methods described herein for avoiding the occurrence of one or more side effects which may result from taking the drug or drugs prescribed.

To facilitate compliance with the methods of the present invention, and to minimize the likelihood of the occurrence of a known or suspected adverse side effect from treatment with the prescribed drug or drugs, it is preferable that when prescriptions for the drug are presented to a registered pharmacy, the computer readable storage medium is consulted to retrieve a prescription approval code before the drug is dispensed to the patient. In order for a prescription approval code to be generated, and based upon the patient's risk group assignment, the patient may be required to provide additional information, which may then be entered in the storage medium before approval of the prescription may be provided. For example, the patient may be required to undergo certain diagnostic tests. In a patient with HIV, for example, testing for viral load may be required, both initially and on a periodic basis, so that dosing of the medication may be adjusted, as necessary. The patient may also be required to complete a survey which asks questions probative of the likelihood that the patient is taking other medications, or beginning to exhibit symptoms which may be of importance to the selection and implementation of a therapeutic regimen. Such additional information may be required both before the initiation of treatment and on a periodic basis during treatment, as new prescriptions and prescription refills are generated. Based upon the information provided by the patient, and the results of any diagnostic tests which have been performed, the patient's risk group assignment may stay the sane, or may be changed, as indicated. The patient's risk group assignment may also be changed based upon the length of time the patient has been receiving a given drug or medication.

A periodic patient survey may serve both to remind the patient of the requirements of the drug distribution program, and to obtain information which may be probative of the risk that an adverse side effect may occur. For example, the survey may include questions probative of the patient's behavior as it relates to the sharing of medication with other HIV positive individuals, and the patient's compliance with measures for avoiding the spread of the disease. Additionally, the survey may include questions regarding other drugs, medications or treatments which the patient might be availing themselves of, which would impact the risk of an adverse side effect occurring.

The survey may also contain questions which are probative of the onset of certain symptoms which may be indicative of the need for changes in the patient's treatment regimen. For example, some questions may be probative of the onset of depression in the patient, a common occurrence amongst AIDS sufferers. Answers to questions in the survey that are indicative of depression, for example, may cause the patient's risk group assignment to change such that the patient is directed to return to the prescriber for determination of whether treatment with an anti-depressant drug is indicated. Similarly, certain drugs, such as protease inhibitors, for example, may lead to abnormal redistribution of fat in certain patients. This symptom may be seen in conjunction with certain metabolic defects and may in turn be symptomatic of conditions such as high blood sugar and high cholesterol. Questions relating to this abnormality may be included on the survey, and answers which indicate that the patient has noticed such physical changes may lead to the assignment of the patient to a risk group in which diagnostic tests probative of the metabolic abnormalities are required before further access to the drug in question is permitted.

As with the survey, the diagnostic testing which the patient may be required to undergo may vary with, and preferably is appropriate to, the patient's risk group assignment. In addition to testing for the patient's viral load, periodic diagnostic testing may be appropriate, for example, to evaluate the level of one or more medications in the patient. Dosage of reverse transcriptase inhibitors, for example, may be critical to the risk of occurrence of an adverse side effect. At the same time, various drugs which are often used in combination may share similar metabolic pathways, so that the addition of a second drug to the treatment regimen may greatly affect the pharmacokinetics of the first drug, thereby necessitating an adjustment in the dose of the first drug. In the case of treatment with an "AIDS cocktail" containing, for example, the use of ritonavir, a well-known protease inhibitor, may greatly impact the bioavailability of other protease inhibitors, requiring that the dose of the other protease inhibitors be reduced. Accordingly, the inclusion of ritonavir in the patient's treatment regimen may initiate a change in risk-group assignment, which in turn requires that diagnostic testing to evaluate the blood levels of other concomitantly administered protease inhibitors be done on a periodic basis.

Similarly, the addition of other drugs to the treatment regimen, either by the prescribing physician, or by another physician whom the patient might visit, may interfere with the initial treatment regimen prescribed by the registered prescriber. For example, AIDS patients often develop mycobacterial infections such as tuberculosis. An infectious disease specialist may prescribe one of a class of drugs known as rifamycins, such as rifampin or rifabutin, to treat such infections. Rifamycins are known to accelerate the metabolism of many protease inhibitors, however, so that upon initiation of treatment with a rifamycin, the effectiveness of the protease inhibitors may be greatly reduced, unless the dosage of those drugs is adjusted appropriately. Thus, when the patient is being treated with a protease inhibitor, the survey may include, for example, questions regarding the possible concurrent use of a rifamycin. If the survey results indicate that the two types of drugs are being used concurrently, the patient's risk group assignment is changed, such that the patient may be referred back to the prescriber for an adjustment in dosage, or the patient may be directed to undergo diagnostic testing to assure that a sufficient level of the protease inhibitor is still being maintained. Similarly, where the registered prescriber adds a prescription for a rifamycin to the treatment regimen of a registered patient who is also receiving a protease inhibitor, entry of the prescription into the computer readable storage medium may trigger an automatic change in risk group assignment, such that approval of the prescription will not be generated without further modification of the dosage of the protease inhibitor. In this way, the methods of the present invention may be advantageously utilized to maintain the proper dosing of one or more drugs, to minimize the likelihood of the occurrence of an adverse side effect from the concomitant use of such drugs, or the addition of other drugs to a treatment regimen, to encourage proper disclosure of the risks associated with the taking of one or more drugs, to minimize the risk that a contraindicated individual will be exposed to the potentially hazardous drugs, and to assist in generating patient compliance with treatment protocols and avoidance of behavior known to increase the risk that the disease will be spread to others.

Various modifications of the invention, in addition to those described herein, will be apparent to those skilled in the art from the foregoing description. Such modifications are also intended to fall within the scope of the appended claims.

What is claimed:

1. A method for delivering a drug to patients in need of the drug while restricting access to the drug by patients for whom the drug may be contraindicated, said method comprising permitting prescriptions for the drug to be filled by a pharmacy only after the pharmacy has received an approval code for the prescription from a computer readable storage medium, wherein generation of the prescription approval code comprises the following steps:

a. defining a plurality of patient risk groups based upon a predefined set of risk parameters for the drug;

b. defining a set of information to be obtained from the patient, which information is probative of the risk that an adverse side effect is likely to occur if the drug is taken by the patient;

c. in response to the information set, assigning the patient to at least one of the risk groups and entering the patient, the information and the patient's risk group assignment into the medium;

d. based upon the information and the risk group assignment, determining whether the risk that the adverse side effect is likely to occur is acceptable; and e. upon a determination that the risk is acceptable, generating the prescription approval code to be received by the pharmacy before the prescription is filled.

2. A method according to claim 1 further comprising registering in the medium the physician who prescribed the drug.

3. A method according to claim 1 further comprising registering the pharmacy in the medium.

4. The method of claim 1 further comprising counseling the patient as to the risks of taking the drug and advising the patient as to risk avoidance measures, in response to the risk group assignment.

5. The method of claim 4 wherein the counseling comprises full disclosure of the risks.

6. The method of claim 5 wherein the prescription is filled only following the full disclosure and informed consent of the patient.

7. The method of claim 6 wherein the informed consent is registered in the computer readable storage medium prior to generation of the prescription approval code.

8. The method of claim 7 wherein the risk group assignment and the informed consent is transmitted to the computer readable storage medium by facsimile and interpreted by optical character recognition software.

9. The method of claim 1 wherein the set of information comprises the results of diagnostic testing.

10. The method of claim 9 wherein the diagnostic testing comprises genetic testing.

11. The method of claim 9 wherein the diagnostic testing is probative of the onset of the adverse side effect.

12. The method of claim 9 wherein the diagnostic testing is probative of the presence of a condition or disease for which the drug is contraindicated.

13. The method of claim 1 wherein the side effect is likely to arise in the patient.

14. The method of claim 1 wherein the side effect is likely to arise in a foetus carried by the patient.

15. The method of claim 1 wherein the side effect is likely to arise in a recipient or a foetus carried by a recipient of the bodily fluid of the patient.

16. The method of claim 15 wherein the recipient is a sexual partner of the patient.

17. The method of claim 1 further comprising:
f. defining for each risk group a second set of information to be collected from the patient at periodic intervals;
g. obtaining the second set of information from the patient; and
h. entering the second set of information in the medium.

18. The method of claim 17 wherein the second set of information comprises a survey regarding the patient's behavior and compliance with the risk avoidance measures.

19. The method of claim 18 wherein the survey is conducted telephonically using an integrated voice response system.

20. The method of claim 17 herein the patient is a female of childbearing potential and the second set of information comprises the results of a pregnancy test.

21. The method of claim 18 wherein the periodic interval comprises about 28 days.

22. The method of claim 1 further comprising providing the patient with a contraceptive device or formulation.

23. The method of claim 1 wherein the adverse side effect comprises a teratogenic effect.

24. The method of claim 23 wherein the drug is thalidomide.

25. The method of claim 23 wherein the teratogenic effect is likely to arise in a foetus carried by the patient.

26. The method of claim 23 wherein the teratogenic effect is likely to arise in a foetus carried by a recipient of the bodily fluid of the patient.

27. The method of claim 26 wherein the recipient of the bodily fluid of the patient is a sexual partner of the patient.

28. The method of claim 26 wherein the set of information includes the results of a pregnancy test.

29. The method of claim 28 wherein the prescription is filled for more than about 28 days.

30. The method of claim 1 wherein the adverse side effect is likely to arise in patients who take the drug in combination with at least one other drug.

31. The method of claim 30 wherein the set of information is also probative of the likelihood that the patient may take the drug and the other drug in combination.

32. The method of claim 30 wherein the set of information includes the results of diagnostic testing.

33. The method of claim 32 wherein the diagnostic testing comprises testing for evidence of the use of the other drug.

34. The method of claim 32 wherein the diagnostic testing comprises testing for evidence which is indicative of the onset of the adverse side effect.

* * * * *

UNITED STATES PATENT AND TRADEMARK OFFICE
CERTIFICATE OF CORRECTION

PATENT NO. : 6,755,784 B2
DATED : June 29, 2004
INVENTOR(S) : Bruce A. Williams and Joseph A. Kaminski It is certified that error appears in the above-identified patent and that said Letters Patent is hereby corrected as shown below:

Column 20,
Line 20, cancel the text "filled for more than about 28 days." and insert -- filled for no more than about 28 days. --.

Signed and Sealed this

Third Day of May, 2005

JON W. DUDAS
*Director of the United States Patent and Trademark Office*